US008784633B2

(12) United States Patent
Xiang et al.

(10) Patent No.: US 8,784,633 B2
(45) Date of Patent: Jul. 22, 2014

(54) AUTOMATIC POSITIONING AND SENSING MICROELECTRODE ARRAYS

(75) Inventors: Guangxin Xiang, Beijing (CN); Liangbin Pan, Beijing (CN); Wanli Xing, Beijing (CN); Lihua Huang, Beijing (CN); Zhongyao Yu, Beijing (CN); Jing Zhu, Beijing (CN); Yuxiang Zhou, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 390 days.

(21) Appl. No.: 12/667,507

(22) PCT Filed: Jul. 4, 2007

(86) PCT No.: PCT/CN2007/002068
§ 371 (c)(1),
(2), (4) Date: Jun. 22, 2010

(87) PCT Pub. No.: WO2009/003315
PCT Pub. Date: Jan. 8, 2009

(65) Prior Publication Data
US 2010/0270176 A1 Oct. 28, 2010

(51) Int. Cl.
*G01N 27/447* (2006.01)
*G01N 27/453* (2006.01)

(52) U.S. Cl.
USPC .......................................... 204/643; 204/547

(58) Field of Classification Search
USPC ............... 204/547, 643; 435/461, 470, 173.6, 435/285.2
See application file for complete search history.

(56) References Cited

U.S. PATENT DOCUMENTS

| 6,448,794 B1 * | 9/2002 | Cheng et al. .................. 324/693 |
| 6,905,586 B2 | 6/2005 | Lee et al. |
| 7,425,253 B2 * | 9/2008 | Voldman et al. .............. 204/547 |
| 2002/0088712 A1 | 7/2002 | Miles |
| 2004/0211727 A1 | 10/2004 | Loock et al. |

FOREIGN PATENT DOCUMENTS

| CN | 1131744 | 9/1996 | |
| CN | 1427255 | 7/2003 | |
| GB | 2386949 A * | 10/2003 | ............. G01N 27/27 |
| WO | WO 03/087293 A1 * | 10/2003 | ............... C12M 1/34 |
| WO | WO-2007/041293 | 4/2007 | |

OTHER PUBLICATIONS

International Search Report for PCT/CN2007/002068, mailed on Apr. 17, 2008, 3 pages.
International Preliminary Report on Patentability for PCT/CN2007/002068, issued on Jan. 5, 2010, 5 pages.

* cited by examiner

*Primary Examiner* — Alex Noguerola
(74) *Attorney, Agent, or Firm* — Morrison & Foerster LLP

(57) ABSTRACT

A microelectrode sensing device includes a substrate and an array of microelectrode sensors. Each sensor includes a first conductive layer that at least partially conducts electricity. The first conductive layer is formed above the substrate and patterned to include a recording electrode that measures electrical activities of target cells. Each sensor also includes a second conductive layer that at least partially conducts electricity. The second conductive layer is elevated above the first layer and patterned to include multiple positioning electrodes arranged to define a sensing region above the recording electrode. The positioning electrodes are designed to generate an electric field pattern in the sensing region to move and confine the target cells to a sub-region of the sensing region that at least partially overlaps the recording electrode.

43 Claims, 10 Drawing Sheets

AUTOMATIC POSITIONING AND SENSING MICROELECTRODE ARRAYS

CROSS-REFERENCE TO RELATED APPLICATIONS

This application is the national phase of PCT application PCT/CN2007/002068 having an international filing date of Jul. 4, 2007. The content of the above-listed PCT application is incorporated herein by this reference in its entirety.

TECHNICAL FIELD

This application relates to microelectrode arrays.

BACKGROUND

Microelectrode arrays (MEAs) can be used for electrophysiological measurements of excitable cells, such as neuronal cells. Electrophysiological measurements can be obtained under various conditions. For example, pharmacological studies can be performed by applying various chemical compounds onto the neuronal cells and recording the resultant electrical activities.

In various electrophysiological measurements, higher amplitude of electrophysiological signals and improved effectiveness of stimulation can be achieved by positioning neurons on or closely in the neighborhood of a recording/stimulation site. Attempts to provide such controlled positioning of neuronal cells by employing physical containment such as micro-wells and micro-channels and/or appropriate materials for surface patterning have been mostly unsatisfactory.

SUMMARY

Techniques, apparatus and systems for automatically positioning cells and recording from the positioned cells using microelectrode arrays are disclosed.

In one aspect, a microelectrode sensing device includes a substrate and an array of microelectrode sensors formed on the substrate. Each sensor includes a first conductive layer, that at least partially conducts electricity, formed above the substrate and patterned to include a recording electrode to measure electrical activities of one or more target cells in a solution. Each sensor also includes a second conductive layer, that at least partially conducts electricity, elevated above the first layer and patterned to include multiple positioning electrodes arranged to define a sensing region above the recording electrode in which the solution is located. The positioning electrodes are designed to generate an electric field pattern in the sensing region to move and confine the target cells to a sub-region of the sensing region that at least partially overlaps the recording electrode.

Implementations can optionally include one or more of the following features. The sub-region can include locations of minimal electrical field strength. Also, the sub-region can be located substantially near a center of the sensing region. Also, at least four positioning electrodes can be included in the microelectrode sensing device. Four of the positioning electrodes can form a first pair of electrodes and a second pair of electrodes designed to apply a first signal and a second signal to generate the electric field pattern. Further, the positioning electrodes can be designed to expose the target cells in the sensing region to one or more dielectrophoretic forces that are generated based on the electric field pattern. The first and second signals can include a pair of alternating current signals, and the one or more dielectrophoretic forces generated can include a negative dielectrophoretic force. Also, the first and second pairs of electrodes can be designed to apply the negative dielectrophoretic force to confine the target cells into a ordered pattern of cells. The pair of alternating current signals can include a signal with an amplitude of 2 volts and a frequency of 5 megahertz. Further, the pair of alternating current signals applied can be separated by a phase angle difference of 180 degrees.

Implementations can also optionally include one or more of the following features. The positioning electrodes can be designed to generate electrical potentials based on a second-order polynomial that obeys Laplace's equation. Also, the positioning electrodes can have a shape based on equipotential boundaries determined based on the generated electrical potentials. Further, the first conductive layer and the second conductive layer can be arranged to reduce capacitive or inductive interference. In addition, one or more passivation layers can be arranged to form barriers that at least partially confine the solution within the sensing region. The positioning electrodes can also be designed to apply signals that selectively lyse one or more of the target cells. Alternatively, each of the sensors in the array can be designed to move and confine the target cells independent of other sensors in the array. Also, the recording electrode can be designed to apply a positive dielectrophoretic force. Further, a signal generator can be included to apply one or more signals through the positioning electrodes or the recording electrode.

In another aspect, a microelectrode sensing device is provided by forming a recording electrode in a first conductive layer, that at least partially conducts electricity, over a substrate. Also, multiple positioning electrodes are arranged in a second conductive layer, that at least partially conducts electricity, over the recording electrode to define a sensing region over the recording electrode and reduce capacitive or inductive interference. Further, a passivation material is added at least between the first and second conductive layers arranged to retain one or more target cells in a solution. Also, the positioning electrodes are used to apply an electric field pattern that moves and confines the target cells to a sub-region of the sensing region that at least partially overlaps the recording electrode. Further, the recording electrode are used to record electrical activities of the confined cells.

Implementations can optionally include one or more of the following features. Moving and confining the target cells can include moving and confining the target cells to a sub-region that includes locations of minimal electrical field strength. In addition, moving and confining can include moving and confining the target cells substantially near a center of the sensing region. Also, at least four positioning electrodes can be arranged to define a sensing region. A pair of sinusoidal signals can be applied to generate the electric field pattern. Also, the target cells in the sensing region can be exposed to one or more dielectrophoretic forces that are generated based on the electric field pattern. Applying a pair of sinusoidal signals can include applying a pair of alternating current signals, and the target cells can be exposed to one or more dielectrophoretic forces including a negative dielectrophoretic force. Further, the target cells can be exposed to a negative dielectrophoretic forces to enable the target cells to form an ordered network of cells. Also a pair of sinusoidal signals can be selected to have a phase angle difference of 180 degrees.

Implementations can also optionally include one or more of the following features. The positioning electrodes can be arranged to generate electrical potentials based on a second-order polynomial that obeys Laplace's equation. Also, the positioning electrodes can be shaped based on equipotential boundaries of the generated electrical potentials. Further, the microelectrode sensing device can be used to perform at least one analysis selected from a group including impedance spectroscopy analysis, cell poration, and electrochemical analysis of physiological changes. In addition, the microelectrode sensing device can be used to record spontaneous action potentials or evoked action potentials from one or more excitable cells. Recording the spontaneous action potentials or evoked potentials can include recording from neuronal cells or heart cells. Further, a positive dielectrophoretic force can be applied through the recording electrode.

In another aspect, a microelectrode sensing device includes a substrate and an array of microelectrode sensors formed on the substrate. Each sensor includes a first layer formed over the substrate and patterned to include a sensing electrode that measures electrical activities of one or more target cells in a solution above the first layer. Each sensor also includes a second layer elevated above the first layer and patterned to include multiple positioning electrodes arranged to define a sensing region on top of the sensing electrode in which the solution is located. The positioning electrodes are designed to generate an electric field pattern in the sensing region to move and confine the target cells above the sensing electrode. An insulator material is filled between the first and second layers to electrically insulate the sensing electrode from the positioning electrodes. The insulator material is shaped to define at least one channel between the first and the second layers to contain the solution, with the sensing region located in the channel.

Implementations can optionally includes one or more of the following features. At least four positioning electrodes can be included in each sensor. Four of the positioning electrodes can be designed to form a first pair of electrodes and a second pair of electrodes designed to apply a first signal and a second signal to generate the electric field pattern. Also, the target cells in the sensing region can be exposed to one or more dielectrophoretic forces that are generated based on the electric field pattern. The first and second signals can include a pair of alternating current signals, and the one or more dielectrophoretic forces generated can include a negative dielectrophoretic force. The recording electrode is further designed to apply a positive dielectrophoretic force. Also, a signal generator can be provided to apply one or more signals through the positioning electrodes or the recording electrode.

In another aspect, a microelectrode sensing device includes a substrate and an array of microelectrode sensors formed on the substrate. Each sensor includes a first conductive layer, that at least partially conducts electricity, formed above the substrate and patterned to include a recording electrode and multiple positioning electrodes. The recording electrode is designed to measure electrical activities of one or more target cells in a solution. The positioning electrodes are arranged to define a sensing region above the recording electrode in which the solution is located. Also, the positioning electrodes are further designed to generate an electric field pattern in the sensing region to move and confine the target cells to a sub-region of the sensing region that at least partially overlaps the recording electrode.

Implementations can optionally include one or more of the following features. Each sensor can include at least four positioning electrodes. Four of the positioning electrodes can be designed to form a first pair of electrodes and a second pair of electrodes. The first and second pair of electrodes can be designed to apply a first signal and a second signal to generate the electric field pattern. Also, the first and second pair of electrodes can be designed to expose the target cells in the sensing region to one or more dielectrophoretic forces that are generated based on the electric field pattern. The first and second signals can include a pair of alternating current signals, and the one or more dielectrophoretic forces generated can include a negative dielectrophoretic force. In addition, the recording electrode can be designed to apply a positive dielectrophoretic force. Further, a signal generator can be included to apply one or more signals through the positioning electrodes or the recording electrode.

In another aspect, a microelectrode sensing device includes a substrate, and an array of microelectrode sensors formed on the substrate. Each sensor includes a first conductive layer, that at least partially conducts electricity, formed above the substrate. The first conductive layer is also patterned to include a recording electrode designed to measure electrical activities of one or more target cells in a solution. The recording electrode is also designed to generate an electric field pattern in a sensing region above the recording electrode to pull and confine the target cells to a sub-region of the sensing region that at least partially overlaps the recording electrode.

Implementations can optionally include one or more of the following features. The recording electrode can be designed to apply at least one signal to generate the electric field pattern. Also, the target cells in the sensing region can be exposed to one or more dielectrophoretic forces that are generated based on the electric field pattern. Further, the one or more dielectrophoretic forces generated can include a positive dielectrophoretic force. In addition, a signal generator can be provided to apply one or more signals through the recording electrode.

The subject matter described in this specification can be implemented to provide one or more advantages. For example, a microelectrode sensing device can be designed to selectively position the target cells and also record electrical activities from the positioned target cells.

The subject matter described in this specification can be implemented as a method, apparatus and system.

BRIEF DESCRIPTION OF THE DRAWINGS

Like reference symbols and designations in the various drawings indicate like elements.

DETAILED DESCRIPTION

Figure 1A:
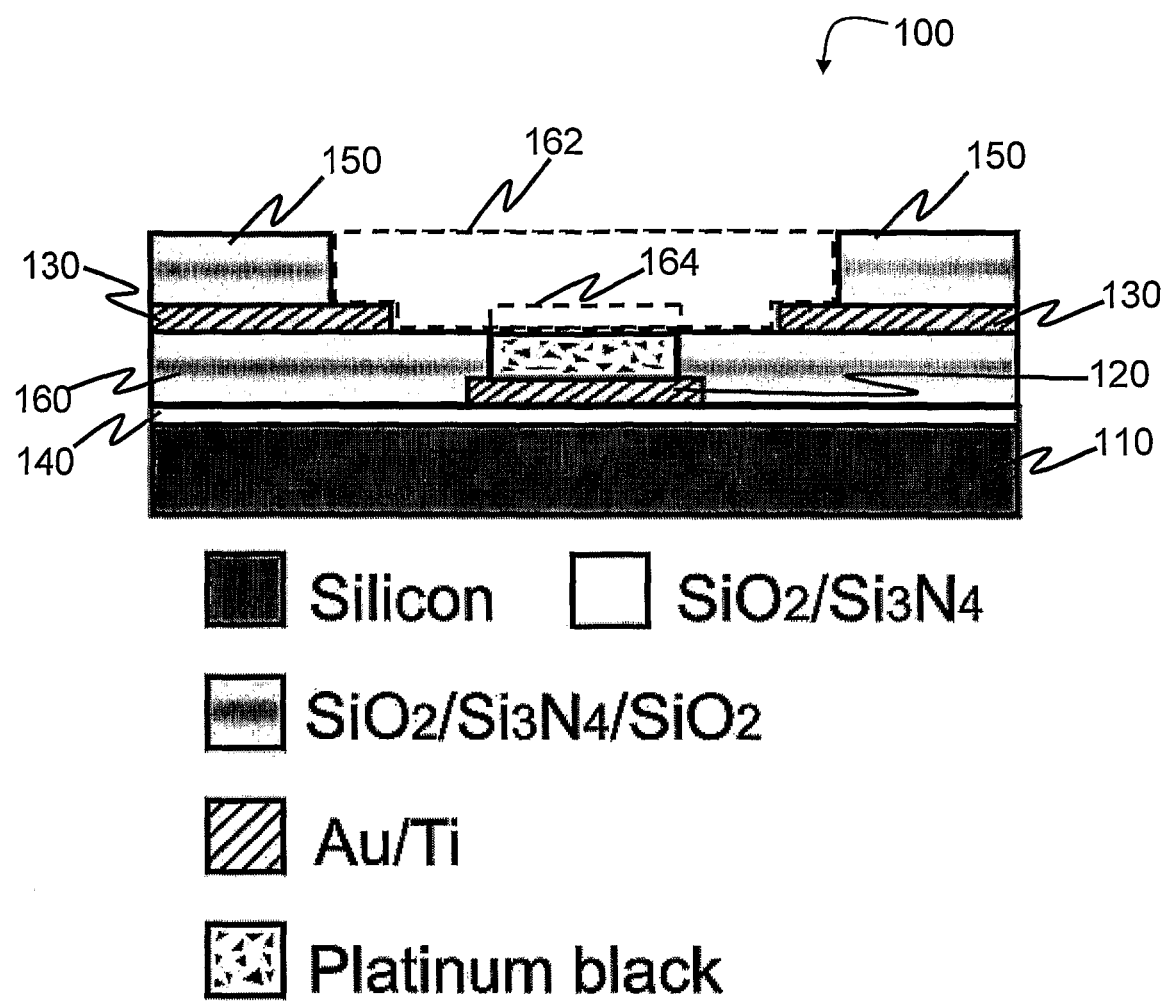
FIG. 1a is a cross-sectional view of a semiconductor device implemented as automatically positioning and sensing microelectrode arrays (APSMEAs).

Dielectrophoretic (DEP) forces can be used to isolate target cells in a predetermined and confined area. When a particle (e.g., a cell) is exposed to a spatially non-uniform electric field, due to the interaction between the electric field and field-induced dipole, a dielectrophoretic force is exerted on the particle. The DEP force, $\vec{F}_{DEP}$, acting on a spherical particle is given by Equation (1):

$$\vec{F}_{DEP} = 2\pi\varepsilon_m R^3 \text{Re}[f_{CM}(\omega)] \cdot \nabla \vec{E}_{rms}^2 \tag{1}$$

where rms represents root-mean-square value of the electric field and Re represents the real part of $[f_{CM}(\omega)]$; and R, $\varepsilon_m$, $\vec{E}$ and $f_{CM}$ represent the radius of the particle, the permittivity of the medium, the electric field strength and the dielectric polarization factor (Clausius-Mossotti factor) of the particle, respectively. Equation (2) below shows the frequency dependence of $f_{CM}$:

$$f_{CM}(\omega) = \frac{\sigma_p^*(\omega) - \sigma_m^*(\omega)}{\sigma_p^*(\omega) + 2\sigma_m^*(\omega)} \tag{2}$$

where $\sigma^*(\omega)=\sigma+j\omega\varepsilon$ and $\omega=2\pi f$; $\sigma^*$ represents the complex conductivity, and index (p) and (m) respectively represent particle and medium; and the variable f represents the frequency of the electric field. When the conductivity of the medium exceeds that of the particle, negative DEP forces are generated and push the particle to a region where the field is minimal.

FIGS. 1a-1d illustrate an example of an microelectrode sensing array device 100 structured to provide automatically positioning and sensing functions based on the above DEP mechanism. In this and other sensing array designs, positioning electrodes (e.g., 132, 134, 136 and 138) are designed to generate the desired negative DEP forces. To control positioning of target cells in a solution, multiple positioning electrodes (e.g., 132, 134, 136 and 138) can be implemented and positioned with respect to one another to define a sensing region in the middle of the positioning electrodes and to form a trapping electric field in this sensing region. When proper voltages are applied to these positioning electrodes, the generated trapping electric field traps the target cells at or substantially near a specific predetermined position. For controlled and predictable applications of DEP forces, the non-uniform electric field distribution established by the shape of the positioning electrodes (e.g., 132, 134, 136 and 138) are determined. The electrode design can be based on an assumption that the electrical potential at any point (x,y) created by the positioning electrodes (e.g., 132, 134, 136 and 138) on the semiconductor device 100 is defined by a second-order polynomial that obeys Laplace's equation as shown in Equation (3)

$$\frac{\partial^2 U(x,y)}{\partial x^2} + \frac{\partial^2 U(x,y)}{\partial y^2} = 0 \tag{3}$$

In Equation (3), U(x,y) represents the potential at point (x,y). The target cells (e.g., neuronal cells) in the inter-electrode space are neutral, and the surface charge density in the interior of trapping area is zero. Substituting a second-order polynomial into Equation (3), U(x, y) can be expressed as shown in Equation (4).

$$U(x,y)=ax^2+bxy-ay^2 \tag{4}$$

In Equation (4), (a) and (b) are independent parameters and U(x, y) is the linear combination of the two independent functions described in Equations (5a) and (5b).

$$U_a(x,y)=x^2-y^2 \tag{5a}$$

$$U_b(x,y)=xy \tag{5b}$$

In Equations (5a) and (5b), $U_a(x,y)$ and $U_b(x,y)$ transpose into each other on interchanging the x–y axes, thus any of them can be used to define equipotentials in the electric field. For example, according to the Equation (5a), the corresponding equipotential boundaries can be determined by Equations (6a) and (6b).

$$x^2-y^2=k \tag{6a}$$

$$x^2-y^2=-k \tag{6b}$$

In Equations (6a) and (6b), k represents the constant for determining the equipotential boundaries. Equations (6a) and (6b) describe the shapes of positive and negative polarities, respectively. The positioning electrodes (e.g., 132, 134, 136 and 138) are shaped according to the equipotential boundaries determined by Equation (6). For example, four of the positioning electrodes (e.g., 132, 134, 136 and 138) can be used to form two pairs of diagonally opposing electrodes in each functional unit 170. When the potentials of +V and −V are applied, the spatial variation of the electric field $|\vec{E}|$ and the DEP force factor $|\nabla \vec{E}^2|$ are given by Equations (7) and (8).

$$|\vec{E}| = 2\frac{V}{k}(x^2+y^2)^{\frac{1}{2}} \tag{7}$$

$$|\nabla \vec{E}^2| = 8\left(\frac{V}{k}\right)^2 (x^2+y^2)^{\frac{1}{2}} \tag{8}$$

While implementing positioning electrodes having a shape based on equipotential boundaries are helpful to the effectiveness of the positioning, such shape is not required. In some implementations, other shapes such as round boundaries can be also used.

FIG. 1a is a cross sectional view of the semiconductor device 100 implemented as automatically positioning and sensing microelectrode arrays (APSMEAs). The semiconductor device 100 includes a substrate 110, a first conductive layer 120 and a second conductive layer 130. The first and second conductive layers 120 and 130 are designed to at least partially conduct electricity. The first conductive layer 120 can include one or more recording or sensing electrodes for measuring electrical activities from target cells in a solution that have adhered to a surface near the sensing electrode 122.

The second conductive layer 130 can include one or more positioning electrodes that define a sensing region 163 above the first conductive layer 120. The positioning electrodes are designed to generate a non-uniformed electric field pattern that causes DEP forces to be applied to target cells in a solution. The DEP forces move and confine particles such as the target cells to a predetermined sub-region 164 in the sensing region 162. The sub-region 164 includes locations in the sensing region 162 with minimal electric field strength, which is harmless to the target cells. In addition, the positioning electrodes and the recording electrodes are arranged to allow the sub-region 164 to substantially overlaps a recording electrode of the first conductive layer 120 located below the second conductive layer 130. Further, the sub-region 164 can be located substantially near a center of the sensing region 162.

The first conductive layer 120 and the second conductive layer 130 are spaced apart in such a manner to reduce or minimized interference due to noise (e.g., capacitive and/or inductive interferences). In particular, when signals of high frequencies are applied through the electrodes (the positioning and/or recording electrodes), capacitive and inductive interference can be generated. In one aspect, by having the first conductive layer 120 and the second conductive layer 130 arranged in different layers (e.g., different horizontal planes), such interferences can be reduced or minimized.

While FIG. 1a shows the first conductive layer having the sensing electrodes and the second conductive layer having the positioning electrodes, the first and second conductive layers can include either of the sensing electrodes and the positioning electrodes. For example, in some implementations, the first conductive layer can include the positioning electrodes and the second conductive layer can include the sensing electrodes.

In some implementations, the semiconductor device 100 is fabricated with the recording electrodes and positioning electrodes in a single layer. When a single layer is implemented, the recording electrode and the positioning electrodes can be electrically insulated by filling an insulating material such as silicon between the electrodes. Alternatively, when a single layer is used, only one type of electrodes may be used. For example, the recording electrode can be used to both record electrical signals (e.g., spontaneous and evoked potentials) from the target cells and apply trapping DEP forces. In such implementations, the recording electrodes apply one or more positive DEP forces to pull the target cells to the recording electrode.

In addition, the semiconductor device 100 includes passivation layers 150 and 160 arranged between the first and second conductive layers 120 and 130 and above the second conductive layer 130. The passivation layers 150 and 150 can also be arranged to separate (e.g., insulate) the conductive layers 120 and 130, which assist in reducing capacitive and inductive interferences.

The semiconductor device 100 implemented as APSMEAs can be produced using a conventional semiconductor process and subsequently encapsulated. The substrate (base layer) 110 can be implemented using a wafer made from a semiconductor material (e.g., silicon) or other materials. On the polished side of the silicon layer 110, an electric insulator layer 140 is applied. The insulator layer 140 can include various combination of layers. For example, a layer of silicon dioxide ($SiO_2$), a layer of silicon nitride ($Si_3N_4$) or both can be applied.

An insulator layer, such as $SiO_2$ or silica, can be grown on the silicon wafer layer 110, for example, by thermal oxidation. Silica possesses high chemical stability, and in electrical applications, silica can protect the silicon layer 110, store charge, block current, and even act as a controlled pathway to allow small currents to flow through a device. $Si_3N_4$ is also an insulator layer that can electrically isolate different structures or act as an etch mask in bulk micromachining. In some implementations, a layer of $SiO_2$ (e.g., with a thickness of 3000 Å) is grown on the polished side of the silicon layer 110 by thermal oxidation, followed by a layer of $Si_3N_4$ (e.g. with a thickness of 1500 Å) using low pressure chemical vapor deposition (LPCVD) process.

The first conductive layer 120 is formed by sputtering a conductive layer, such as a gold/titanium (Au/Ti) film with a predetermined thickness (e.g., Au 2000 Å and Ti 200 Å). The electrode structure within the first conductive layer 120 can be created by lift-off technology. Using liftoff technology, a metallization layer can be deposited at high temperature to provide highly packed interconnection metallization.

Using a plasma enhanced chemical vapor deposition (PECVD) process, a triplex layer of $SiO_2/Si_3N_4/SiO_2$ (example thicknesses of 4000 Å/5000 Å/1000 Å) is formed as a passivation layer 160 for the first conductive layer. The second conductive layer 130 is placed above the passivation layer 160. A passivation layer 150 for the second conductive layer 130 is placed above the second conductive layer 130. The passivation layers 150 and 160 (located above the first conductive layer 120 and the second conductive layer 130) and the bonding-pads can be removed by reactive ion etching (RIE).

Figure 1B:
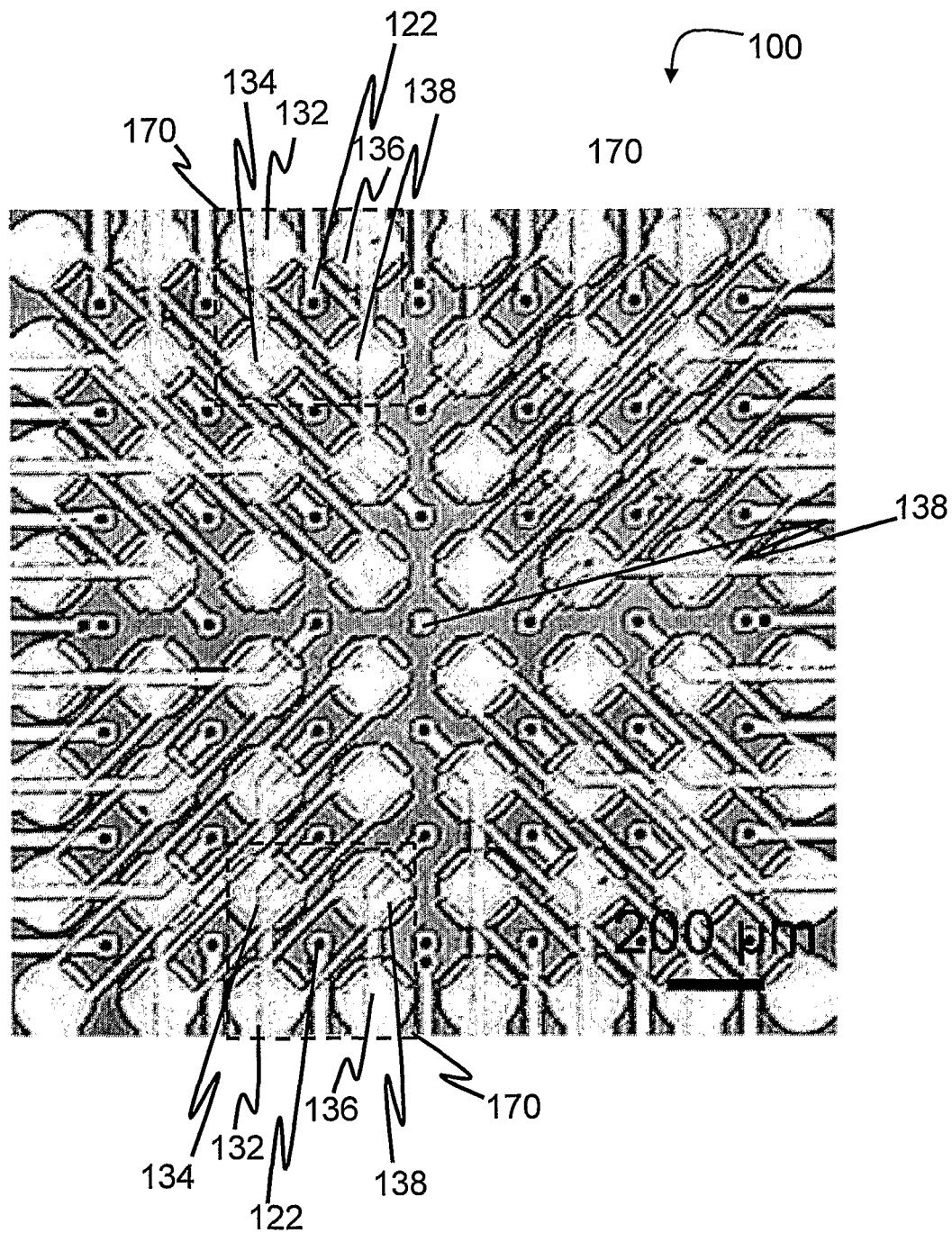
FIG. 1b is a top-down view of a semiconductor device implemented as a APSMEA microchip device.

FIG. 1b is a top-down view of the semiconductor device 100 implemented as a APSMEA microchip device. Using standard microelectronic fabrication technologies, a APSMEA microchip is fabricated. The tight dimensional control of photolithography provides a high reproducibility of manufacture and consistent performance. Within one APSMEA microchip, various numbers of functional units 170 can be included. Each functional unit 170 includes multiple positioning electrodes 132, 134, 136, 138 and one or more recording electrodes 122.

In FIG. 1b, the example APSMEA device 100 shows 48 recording electrodes 122 (20 μm square each) plus one pad located in the center 138, arranged in a matrix of 7×7, with 225 μm center-to-center spacing in between the 48 functional units 170 and one center unit. Including the center unit, 49 groups of DEP electrodes (e.g., four positioning electrodes 132, 134, 136 and 138 make up each DEP electrode group in FIG. 1b) are fabricated with each group surrounding one recording electrode 122. The four positioning electrodes 132, 134, 136 and 138 in each DEP electrode group enable the establishment of DEP traps and thus control movement of target cells to a desired location (e.g., center of the DEP trap). Signals are applied to the positioning electrodes that make up the DEP electrode group to generate negative dielectrophoretic forces. The negative DEP forces push the target cells, loaded in each of the functional units, near or substantially at the center of each functional unit. Alternatively, signals can be applied through the recording electrodes 122 (with other types of signals) to generate positive dielectrophoretic forces. Positive DEP forces can act to directly pull and trap the cells towards the centrally located recording electrodes 122. In some implementations, both negative DEP forces through the positioning electrodes and positive DEP forces through the recording electrodes can be applied together.

The positioning electrodes 132, 134, 136 and 138 in each DEP electrode group and/or the recording electrodes 122 are also shaped according to the equipotential boundaries determined by the curves (xy=±6400), which can facilitate the generation of negative DEP forces as described above. Further, due to the complexity of the array with the combination of the two types of electrodes, the layout of the leads is considered carefully.

In some implementations, the positioning electrodes and/or the recording electrodes are generated using shapes independent of the equipotential boundaries. While implementing positioning electrodes having a shape based on equipotential boundaries are helpful to the effectiveness of the positioning, such shape is not required. For example, other shapes such as round boundaries can be also used.

Each functional unit 170 of the APSMEA semiconductor device 100 includes at least four positioning electrodes 132, 134, 136 and 138 fabricated in the second conductive layer 130. Each functional unit 170 also includes at least a recording electrode 122 fabricated in the first conductive layer 120. The recording electrode 122 is located substantially in the center of the four surrounding positioning electrodes 132, 134, 136 and 138.

In some implementations, the number of positioning electrodes can be varied (i.e., more than four as shown in FIG. 1a-b). For example, 6, 8, 10, or more positioning electrodes can be implemented. In all implementations, at least one recording electrodes are implemented at the center of the multiple positioning electrodes.

Figure 1C:
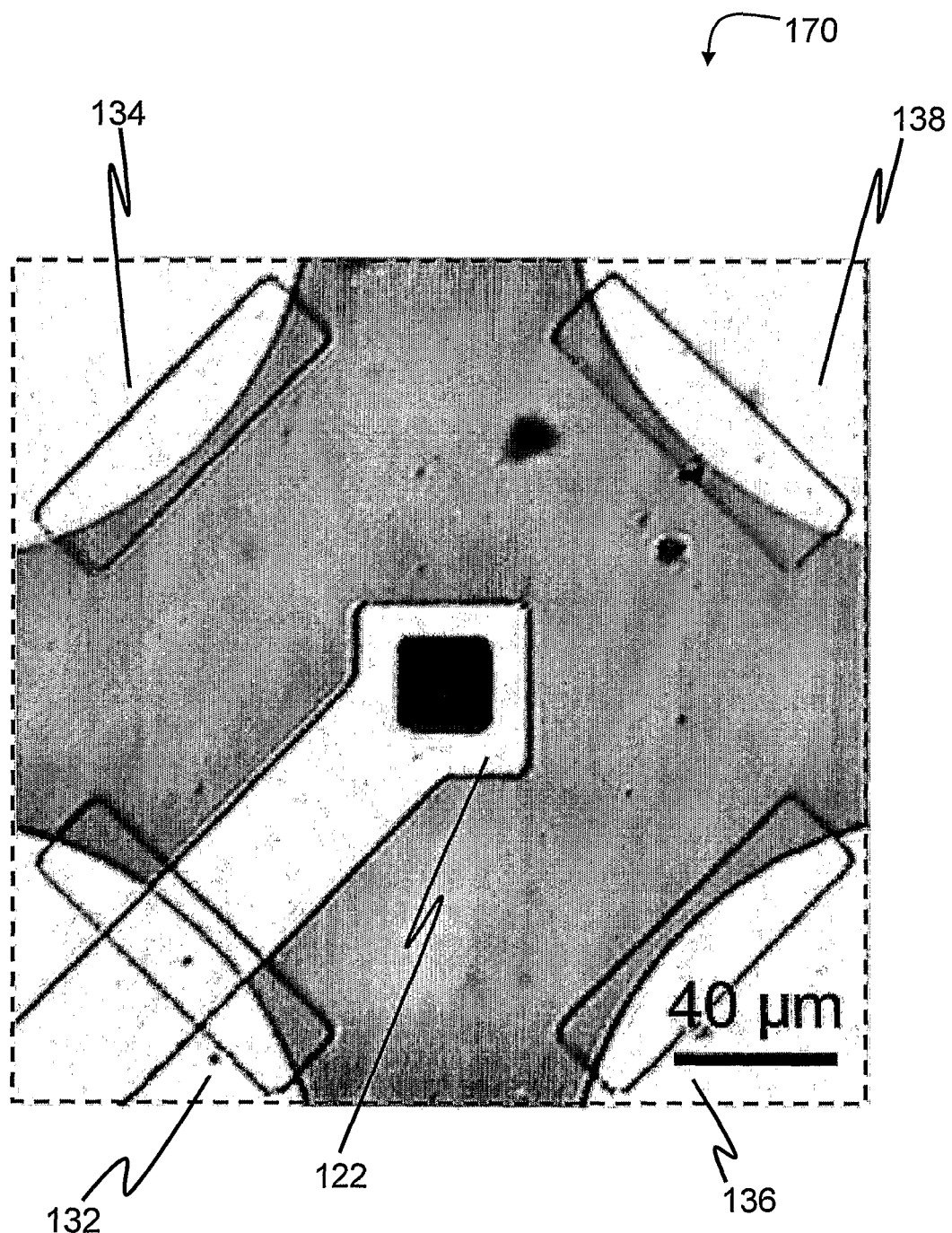
FIG. 1c is a top-down view of one of many functional units available in a APSMEA device.

FIG. 1c is a top-down view of one functional unit 170 of the 48 functional units 170 available in the APSMEA device 100. To enable the establishment of dielectrophoretic traps, multiple groups (e.g., 49 groups not including the one center unit without a functional recording electrode) of positioning electrodes are fabricated to surround the recording or sensing electrodes (e.g., electrode 122.)

The positioning electrodes 132, 134, 136 and 138 can be designed to selectively position cells in one, some or all of the functional units. For example, each functional units can be controlled and/or operated independently to trap cells in selected one or more functional units only. Alternatively, all of the functional units can be controlled and/or operated together to trap cells in all of the functional units.

Figure 1D:
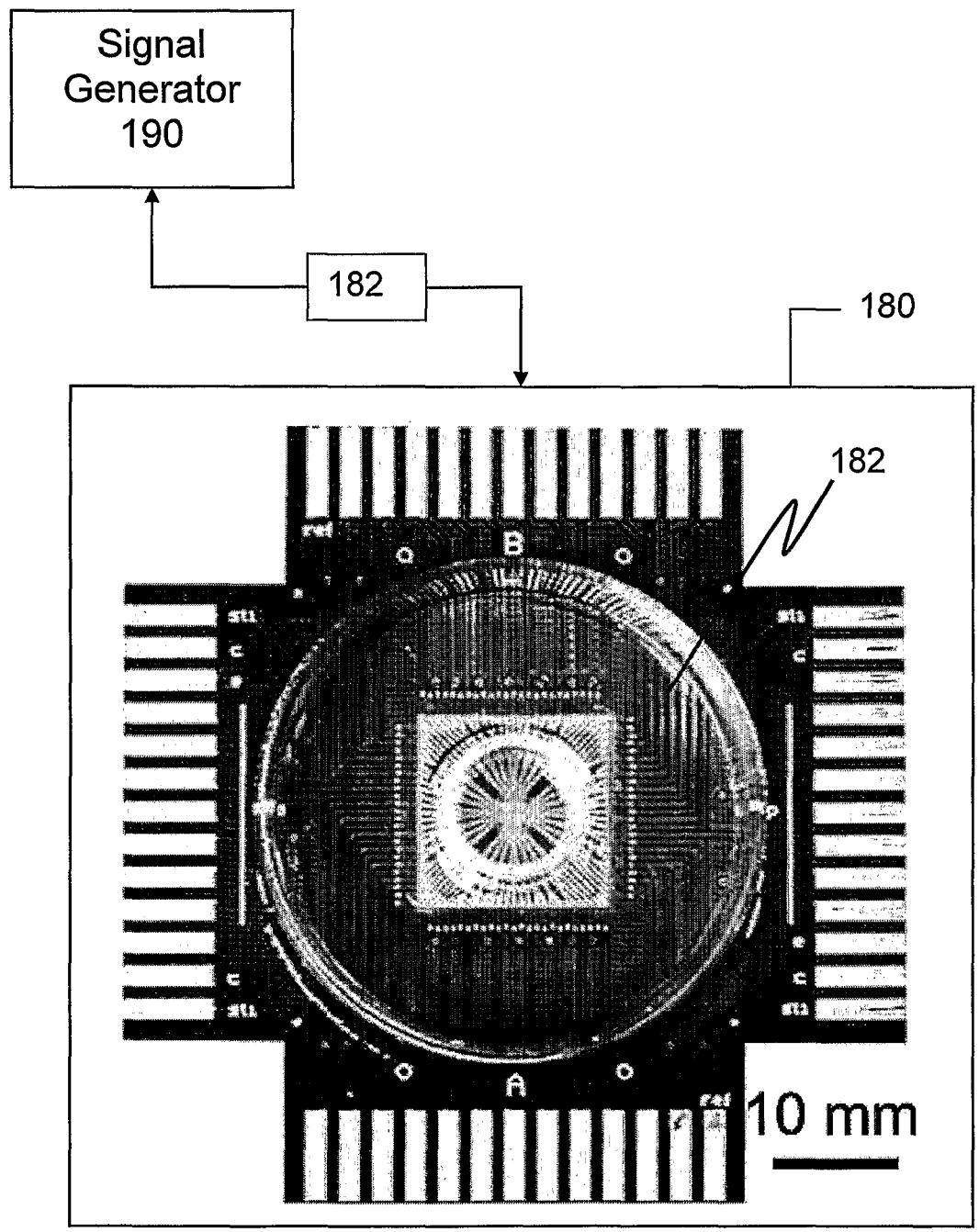
FIG. 1d is a top-down view of a semiconductor device assembled as a functional APSMEA device encapsulated with a printed circuit board (PCB) and a cell culture chamber.

FIG. 1d is a top-down view of the semiconductor device 100 assembled as a functional APSMEA chip 180 encapsulated with a printed circuit board (PCB) with a cell culture chamber. The pads on the PCB are readily connected to a commercial amplifier with zebra strips. For example, a semiconductor device 100 can be diced, and a chip 180 (e.g., 15×15 mm$^2$) can be assembled on a PCB (e.g., 60×60 mm$^2$) by wire bonding. A polystyrene ring (e.g., Φ9 mm) and a plastic petri-dish (e.g., Φ35 mm) 182 with a hole (e.g., Φ11 mm) are positioned on and glued to the chip 180 with Sylgard. The APSEMA chip 180 can be connected to a signal generator 190 using a bidirectional communication 192. The bidirectional communication link 182 can include one or more wired or wireless connections. Wired connections can include Universal Serial Bus connections, FireWire, other serial or parallel connections, etc. Wireless connections can include Bluetooth, Wifi, Wimax, etc.

The signal generator 190 is designed to provide the electrical signals used to apply positive or negative DEP forces through the sensing electrodes 122 and/or positioning electrodes 132, 134, 136 and 138. Further, the signal generator 190 can provide the stimulation signal for measuring evoked potentials from the target cells.

The recording electrodes 122 can be platinized in a solution containing 1% chloroplatinic acid and 0.01% lead acetate at a constant plating voltage of 0.8 volts for 20 seconds. The ohmic component of electrode impedance can be assessed before and after platinization in 0.9% NaCl at 22° C., using a National Instruments S series device (NI-PCI-6110, National Instruments Corp., Austin, Tex.) controlled by Labview-based software with a constant 1 kHz, 0.5 volt signal. Electrochemical platinum plating produced a marked decrease in electrode impedance as low as 50±16 kΩ (n=20, with 4 recording electrodes 122 selected at random from each of 5 APSMEAs), compared with 1.5±0.2 MΩ of unplatinized electrodes (n=20, as above) at 1 kHz, the known frequency scale for neuronal action potentials. The platinum plated on electrodes can serve as an excellent polarizable interface in solution, which consequently decreases the noise and increases the signal/noise ratio.

Figure 2:
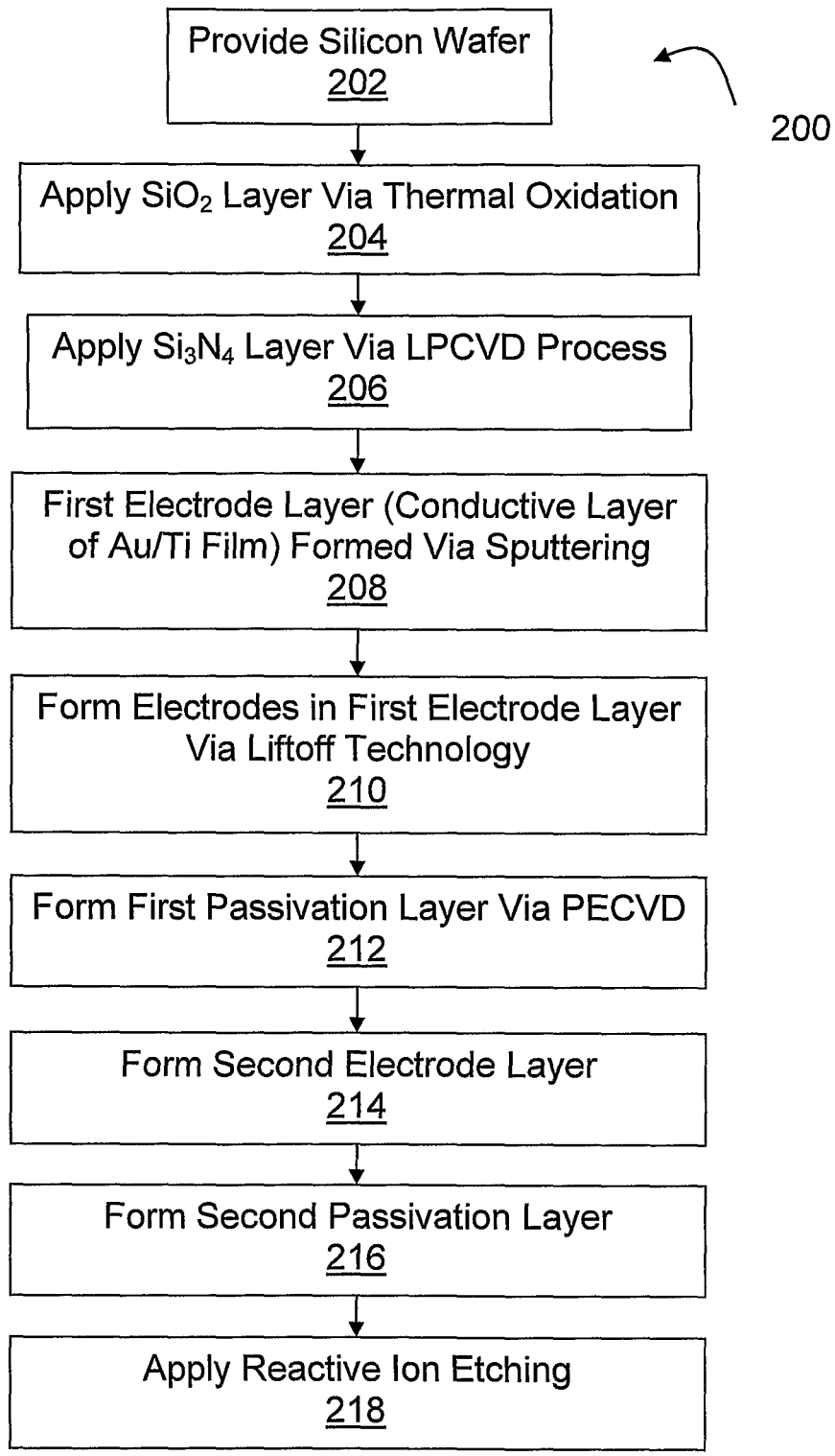
FIG. 2 is a process flow diagram of a process for fabricating a semiconductor device.

FIG. 2 is a process flow diagram 200 of fabricating a semiconductor device such as the device 100. At 202, a silicon wafer is provided. At 204, an electrical insulator (e.g. SiO$_2$) layer is grown on silicon layer by thermal oxidation. Using LPCVD process, a layer of Si$_3$N$_4$ is applied at 206 after SiO$_2$ is applied. At 208, a conductive layer (e.g., first conductive layer 120) of Au/Ti film is formed by sputtering. The electrodes in the first conductive layer 120 are formed by liftoff technology at 210. At 212, a passivation layer for the first conductive layer (e.g., a triplex layer of SiO2/Si3N4/SiO2 with example thickness of 4000 Å/5000 Å/1000 Å) is formed using a plasma enhanced chemical vapor deposition (PECVD) process. The second conductive layer is formed above the first passivation layer at 214. A second passivation layer for the second conductive layer is formed above the second conductive layer at 216. The passivation layers 150 and 160 (located above the conducting surfaces of the first conductive layer 120 and the second conductive layer 130) and the bonding-pads are removed by reactive ion etching (RIE) at 218.

Figure 3:
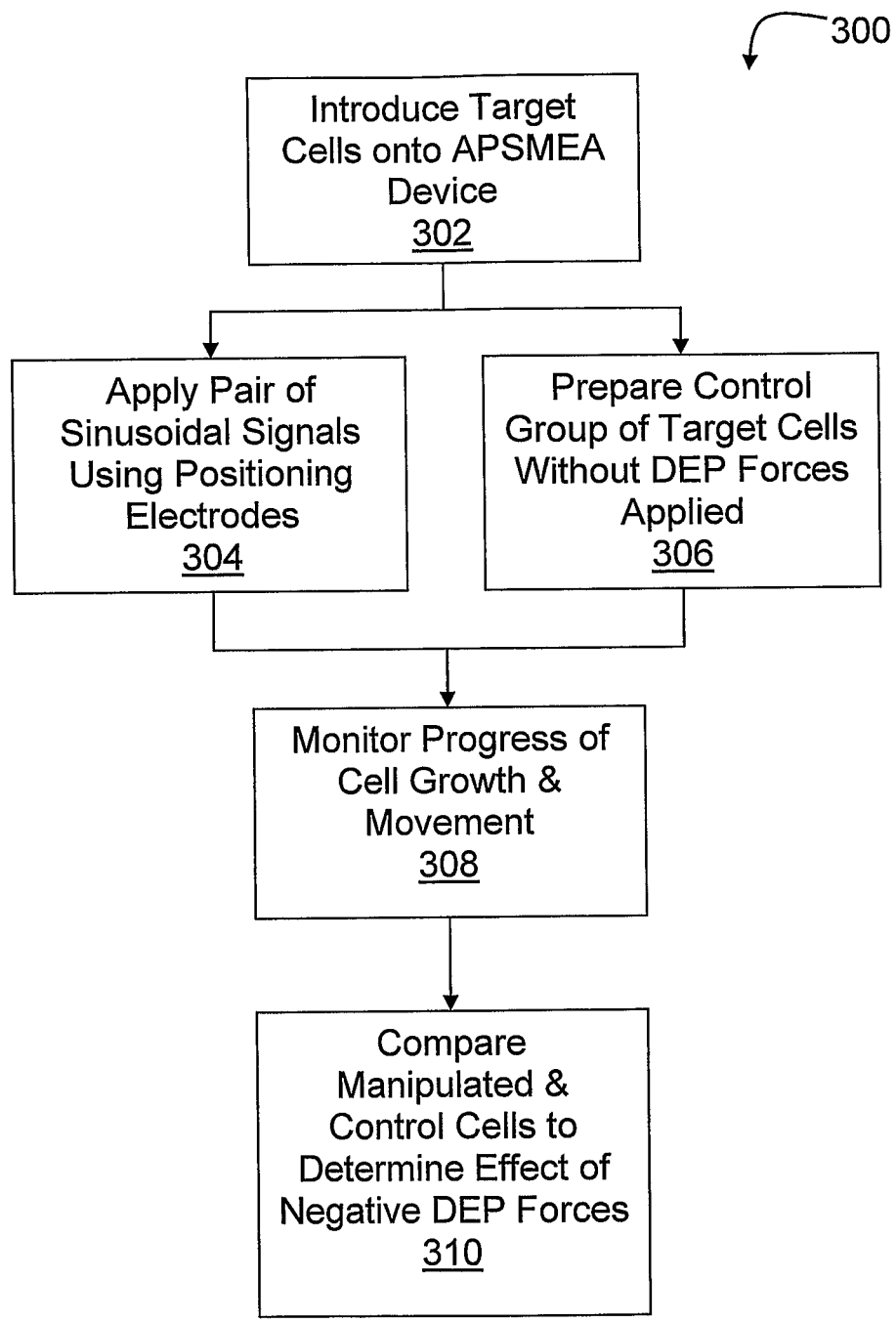
FIG. 3 is a process flow diagram of a process for controlling movement of target cells into a predetermined location using negative DEP forces.

FIG. 3 is a process flow diagram 300 of a process for controlling movement of target cells into a predetermined location using negative DEP forces. At 302, target cells (e.g., neuronal cells) in suspension are introduced onto a APSMEA device 100. The target cells are prepared according to institutional guidelines for care and use of animals. For example, to obtain neuronal cells, cortical neurons are excised from 18-day rat embryos and dissociated by trituration after digestion with papain (20 U/ml). The neurons are then resuspended in Neurobasal medium with B27 supplement and 500 μM glutamine. The medium initially added to new cultures are also supplemented with 25 μM glutamate and 25 μM β-mercaptoethanol. With four different concentrations, i.e., 1×105 cells/ml, 2×105 cells/ml, 5×105 cells/ml and 1×106 cells/ml, neurons are seeded on the APSMEA device 100 after coating with poly-L-lysine (50 μg/ml) and laminin (10 μg/ml).

At 304, the seeded target cells are manipulated by applying a pair of sinusoidal signals using the positioning electrodes (e.g., 132, 134, 136 and 138). The signals applied generate non-uniform electric fields, and the target cells in the generated non-uniform electric fields experience dielectrophoretic forces. Since dielectrophoretic forces are independent of polarity of the electric fields, either alternate current (AC) or direct current (DC) signals can be applied. For instance, AC signals at wide range of frequencies (e.g., 500 Hz to 50 MHZ) can be applied. Further, the applied signals can be applied fore various time periods. In some implementations, a pair of 5 megahertz (MHz), 2 volts (V) sinusoidal signals with a phase-angle difference of 180° are applied for 30 minutes. To determine the effect of DEP forces, a control group of target cells are also prepared on a separate APSMEA device with no signals applied at 306.

At 308, progress of cell growth and movement in the presence and absence of DEP forces are monitored. For example, using an upright microscope in the reflection mode equipped with differential interference contrast optic (DMR/HCS, Leica, Germany), the progress of target cell manipulation can be monitored, and the images from the microscope can be acquired by an imaging device, such as a charge-coupled-device (CCD) video camera (WV-GP410, Panasonic, Japan). Both of the APSMEA devices (control and test) are transferred into a humid, 37° C. and 5% $CO_2$ incubator. The target cells in both devices are fed by changing half of the culture medium twice a week. The movements and growth of cells in DEP forces applied and control cells are compared at 310 to determined the effect of the DEP forces in controlling the movement and isolation of target cells.

Figures 4A, 4B, 4C, 4D, 4E, 4F, 4G, 4H, 4I, 4J:
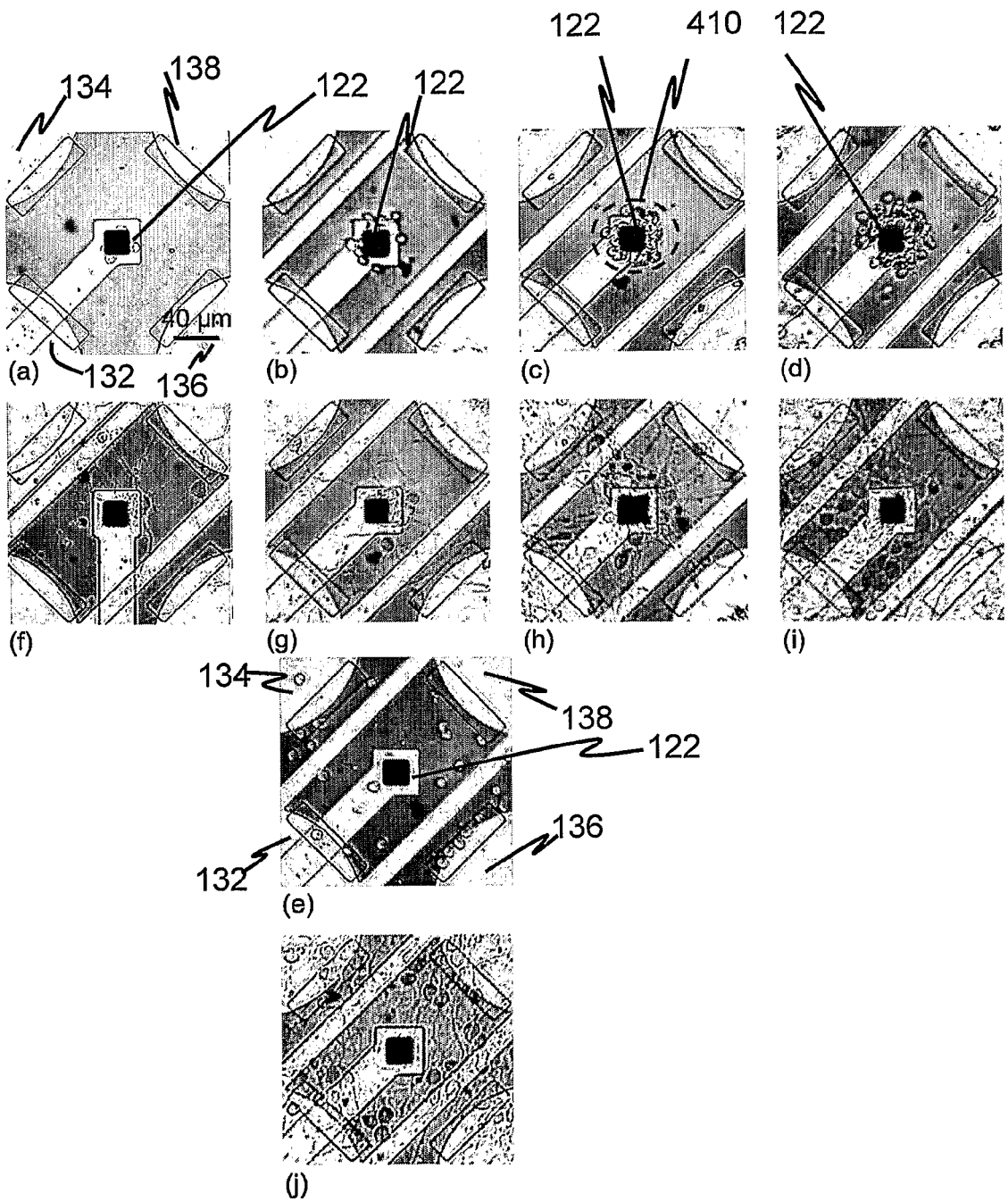
FIGS. 4a-d and 4f-i are images taken using an imaging device that show the positioning of target cells (in these images, neuronal cells) with negative DEP forces applied for 30 minutes at different cell concentrations.
FIGS. 4e and j are images taken using an imaging device that show the positioning of target cells (in these images, neuronal cells) without negative DEP forces applied at cell concentrations of 5×105 cells/ml.

FIGS. 4a-d and 4f-i are images taken using an imaging device that show the positioning of target cells (in these images, neuronal cells) with negative DEP forces applied for 30 minutes at different cell concentrations of (4a & f) $1\times10^5$ cells/ml, (4b & g) $2\times10^5$ cells/ml, (4c & h) $5\times10^5$ cells/ml, and (4d & i) $1\times10^6$ cells/ml, respectively. FIGS. 4f-i represent neuronal cell growth after days of culture corresponding to cell concentrations in FIGS. 4a-d. For example, FIG. 4c shows that DEP forces pushed and positioned the neuronal cells to a predetermined area 410 over the recording electrodes 122 where the electrical field was minimal and harmless to the cells. A very few of neurons were positioned on the recording electrodes 122 at the concentration of $1\times10^5$ cells/ml (FIGS. 4a & f), and the cells accumulated with the increase of cell concentrations (FIGS. 4b-d & and g-i), until a large number of them gathered around the recording electrodes 122 at the concentration of $1\times10^6$ cells/ml (FIGS. 4d & i).

FIGS. 4e & j are images taken using an imaging device that show the positioning of target cells (in these images, neuronal cells) without negative DEP forces applied at cell concentrations of $5\times10^5$ cells/ml. FIG. 4j represents the random growth of the neuronal cells after 3 days (still without negative DEP forces.) In contrast to the negative DEP forces-treated patterns (FIGS. 4a-d & f-i), neuronal cells for the control (FIGS. 4e & j) randomly settled on the APSMEA. Supporting the cell growth, the culture medium used during the manipulation of neurons need not be changed.

Although it is reasonable that the proportion of the recording electrodes 122 covered with neurons (when DEP forces are applied) started relatively low and gained as time passed, cells are apt to be manipulated at the initial time of being seeded. At the lowest concentration of $1\times10^5$ cells/ml (FIGS. 4a & f), the proportion of cells positioned near or at the recording electrodes 122 arrived at 44.4±12.7% after applying negative DEP forces for only 5 minutes, and finally 76.4±9.8% for 30 minute application of DEP forces (n=4, separate APSMEAs). At the concentration of $1\times10^6$ cells/ml (FIGS. 4d & i), each of the recording electrodes 122 in a APSMEA device 180 possessed at least one cell localized at or near the recording electrode 122 after 5 minutes of DEP application without exception.

Continuation of the DEP forces for longer durations resulted in congregation of cells over each recording electrode 122 (n=4, as above). At the concentrations of $2\times10^5$ cells/ml (FIGS. 4b & g) and $5\times10^5$ cells/ml (FIGS. 4c & h), the proportions of cells localized at or near the recording electrode 122 were 88.2±3.2% and 99.5±1.0% after 30 minutes of DEP forces applied (n=4, as above), respectively.

Figure 5A:
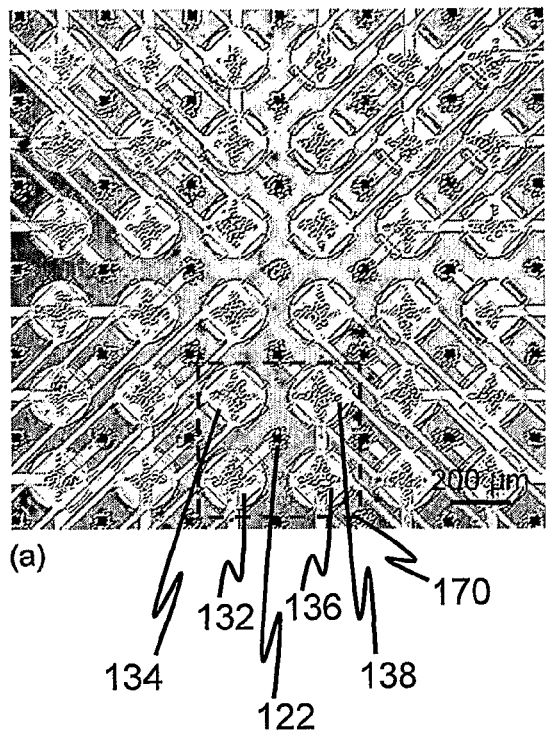
FIGS. 5a and 5b show a top-down view of recording electrodes with neurons positioned at or near the recording electrodes at cell concentration of 5×105 cells/ml.
Figure 5B:
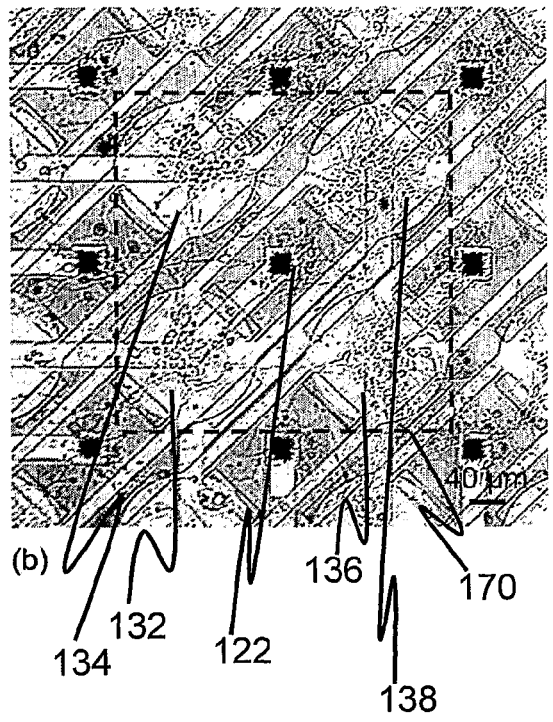

FIGS. 5a & 5b show a top-down view of all the recording electrodes 122 with neurons positioned at or near the recording electrodes 122 at cell concentration of $5\times10^5$ cells/ml. FIG. 5b represents outgrowth of neurites in vitro after 3-day culture. To facilitate the formation of cellular networks after the outgrowth of neurites, neurons (neuronal cells) also settled down between the groups of DEP electrodes due to the passivation layer maintained there. Taken together, these results show that APSMEAs devices can conveniently and effectively position desired numbers of target cells such as neurons over the recording electrodes 122.

Compared with the control cells with no DEP forces applied (FIG. 4j), the neurites of the positioned neurons (3 DIV) can freely grow out to contact with other neurons while most of their somas retained in position (FIG. 4f-i and FIG. 5b), indicating that APSMEAs devices can ensure the sufficient synapse formation between neurons and maintain the functional activities of neuronal networks during development. The DEP force application using the APSMEA device enables target cells to form an ordered network of cells. In case of neuronal cells, DEP force application results in an ordered neural network. In contrast, control group of cells without DEP forces applied form a random network of cells. Throughout two-week culture period, the neurites can continue to grow dense and the glial cells proliferated, leading the engineered structure of the neuronal networks to become slightly blurred. Further, Glial cells can provide necessary trophic factors for cultured neurons, and that direct contact between neurons and glia can also be crucial for neuronal survival.

Once the cells have be positioned as desired near the centrally located recording electrodes 122, different treatments/analyses can be carried out using the device 100. For example, some of the applicable analyses include impedance spectroscopy analyses, cell poration, and electrochemical analysis of physiological changes.

Figure 6A:
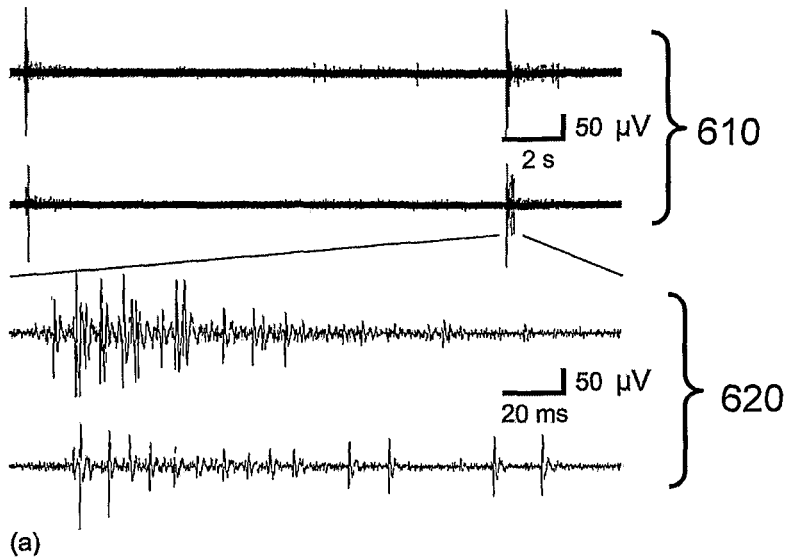
FIG. 6a is a representative recordings of electrical activities.
Figure 6B:
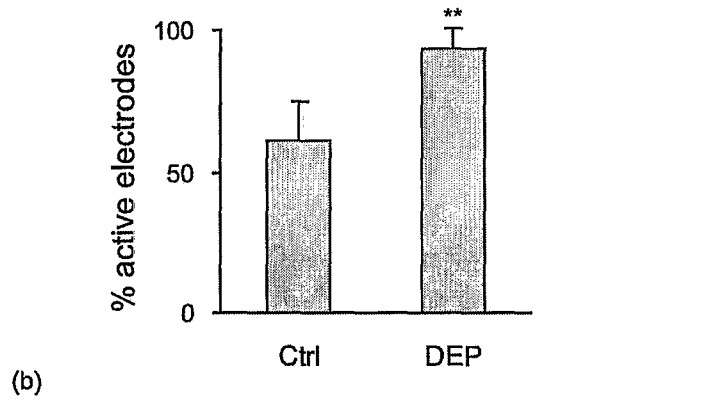
FIG. 6b shows a comparison of the percentage of active recording electrodes within each APSMEA device between control and manipulated cells.
Figure 6C:
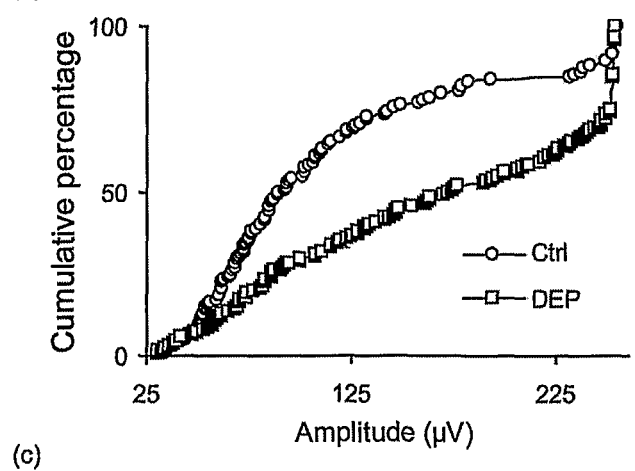
FIG. 6c represents cumulative percentage histograms of the maximal amplitudes of the signals from control and manipulated (DEP forces applied) cells.

FIG. 6a-c represent results of multi-site recordings of extracellular spontaneous electrophysiological activities from cortical neuronal networks (14 DIV) for control (no DEP forces applied) and manipulated (with DEP forces applied) cells at the seeding cell concentration of $5\times10^5$ cells/ml. Multi-site electrophysiological recordings in this and other implementations can be performed with the APSMEA device connected with a commercial multi-channel amplifier and filtering stage (Cyberkinetics, Salt Lake City, Utah). Measurements are carried out in 14 days old cortical cultures at 37° C., allowing the signals from the recording electrodes 122 amplified (×5000), band-pass filtered (250-7500 Hz), and sampled at 30 kHz/channel on 25 channels simultaneously. Using ±3 times of the standard deviation of the noise level as the threshold value for each channel, electrophysiological activities are detected on-line or off-line. NMDA (5 μM) and APV (5 μM) are also applied in the culture medium, and their related electrophysiological activities before and after any drug (e.g., chemical compounds) administration are both recorded for 10 min. The excitatory or inhibitory effect of any drugs applied on neurons are then simply defined as percentage changes in sum of spikes over all the active sites and the time course with drug treatment, compared with that of control (without drug treatment).

FIG. 6a is a representative 20-second long traces recorded with the two electrodes 510 and typical bursts shown on the expanded time scale (0.2-second traces) 520. FIG. 6b shows a comparison of the percentage of active recording electrodes 122 within each APSMEA device between control and manipulated cells (**P<0.01, Student's t-test, n=4). The control cells and the manipulated cells were prepared in separate APSMEA devices. Error bars represent standard deviation. FIG. 6c represents cumulative percentage histograms of the maximal amplitudes of the signals from control (n=117, recording electrodes pooled from 4 separate APSMEAs in FIG. 6b) and manipulated (DEP forces applied) cells (n=180, as above).

The recordings shown in FIG. 6a (and analysis shown in FIGS. 6b & C) are based on single action potentials, usually biphasic or triphasic in shape, recorded using the recording electrodes 122 from DEP forces applied and control cells. These electrical activities are inhibited by 1.5 µM TTX (known to be a blocker of voltage-dependent Na+ channels), verifying the physiological basis for the observed extracellular action potentials (data not shown). In some implementations, the recording electrodes 122 can be also used to stimulate neurons non-destructively (data not shown), providing another application of APSMEAs in neuroscience studies.

Because the extracellular electrophysiological signals with larger amplitudes can be picked up while neurons are closer to the recording electrodes 122, the proportion of electrodes with the electrophysiological signals detected within each APSMEA device was taken into account, as well as the maximal amplitude of the signals from each electrode. As shown in FIG. 6b, 93.8±7.4% of the recording electrodes 122 from DEP applied neuronal networks were active, significantly greater than 60.9±14.2% from control networks (P<0.01; Student's t-test; n=4, separate APSMEAs). With 166.7±78.5 $\mu V_{peak-peak}$ of the maximal amplitude of the signals from DEP networks (n=180, recording electrodes pooled from 4 separate APSMEAs in FIG. 6b) and 116.3±68.0 µVpeak-peak from control (ctrl) networks (n=117, as above), the cumulative percentage histograms also showed the significant differences between DEP and Ctrl networks (P<0.001; two-sample Kolmogorov-Smirnov tests), as shown in FIG. 6c. Although it was unavailable to strictly constrain the positioned neurons in their original locations after two-week culture, these results strongly suggest that APSMEAs achieved the improved performance of automatically positioning cells to a predetermined location (over the recording electrodes) and allowing recordings from those isolated cells in MEA-based recordings.

In some implementations, action potentials of positioned neuronal (or other excitable cells such as cardiac myocytes) can be recorded by using the recording electrodes 122. The recording electrodes 122 can measure spontaneously generated action potentials of the positioned excitable cells (e.g., neuronal or cardiac cells). In addition, the recording electrodes 122 can be used to measure evoked potential generated by applying electrical/chemical stimulus to the positioned cells.

Figures 7A, 7B, 7C:
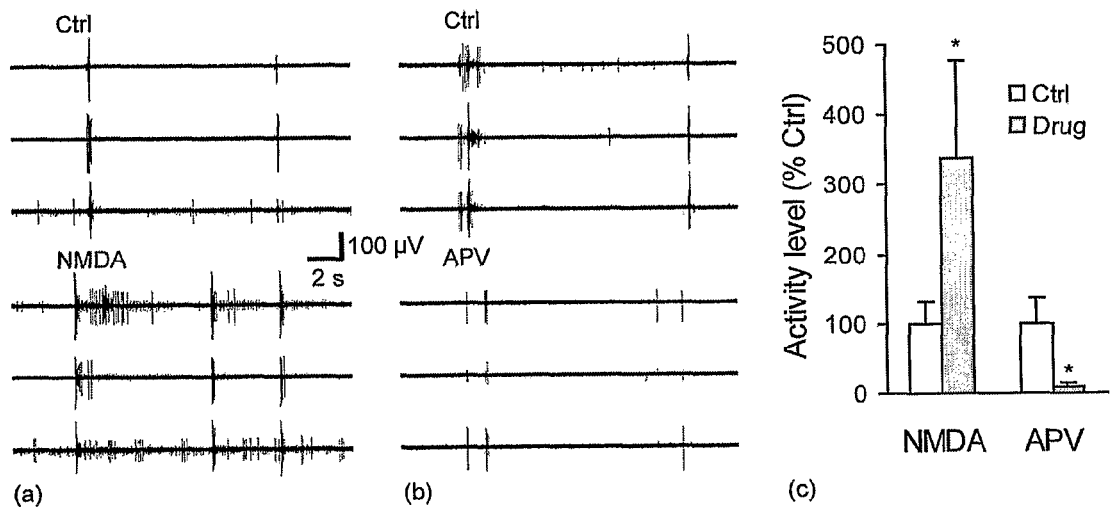
FIGS. 7a-b represent examples of spontaneous activity before and after neurons are treated with 5 µM NMDA and 5 µM APV, respectively.
FIG. 7c represent histograms of NMDA and APV induced-changes in electrical activity level compared with the no drug added control.

FIGS. 7a-c show results of pharmacological evaluations using APSMEAs with cortical neurons (14 DIV). FIGS. 7a-b represent typical examples of spontaneous activity (20-second plot of 3 channels) before and after neurons are treated with 5 µM NMDA and 5 µM APV, respectively. FIG. 7c represent histograms of NMDA and APV induced-changes in electrical activity level compared with the no drug added control (100%). (*P<0.05, Student's t-test, n=4 (separate APSMEAs).) Error bars represent standard deviation.

Based on the multi-site electrophysiological recordings of cell using the APSMEA, the responses of neuronal populations in vitro (14 DIV) during drug administration are monitored. As shown in FIG. 7, the NMDA receptor agonist NMDA (5 µM) triggered the neurons to fire intensively, causing the induced activity level to increase three times more than that of controls (n=4, separate APSMEAs). In contrast, 5 µM APV (NMDA receptor antagonist) drastically decreased the activity level (7.8±7.5% of control; n=4, as above). Application of NMDA and APV showed the excitatory and inhibitory effects on neuronal networks, respectively. Although only such simple information was extracted from the activity patterns at network level, the results with these two typical agents tend to verify the utility of the APSMEA with cortical neurons as a cell-based biosensor in pharmacological applications, and can also bridge the gap between single cell-based analysis and animal experiments.

With the optimized electromotive parameters, the strategically designed DEP electrodes on the APSMEA can effectively position desired numbers of neurons onto multiple recording electrodes simultaneously and without injury. The neurites are then able to grow out freely to form functional synapses while the somas are retained in the defined areas of the APSMEA. The electrophysiological activities of neuronal networks examined by the recording electrodes (see, FIGS. 6a-c and 7a-c) demonstrate the marked improvement of the APSMEA in performance and its utility in pharmacological applications.

The convenience and effectiveness of such a system can stimulate the use of APSMEA devices, facilitating a better understanding of the function of neuronal networks in vitro and pharmacological evaluation at network level. The techniques of applying DEP forces described in this specification are not restricted to neurons, and can satisfy many specific needs for the manipulation and positioning of different kinds of cells for a variety of desired evaluations.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments, and it should be understood that the described components and systems can generally be integrated together in a single system or apparatus.

Only a few implementations and examples are described and other implementations, enhancements and variations can be made based on what is described and illustrated in this application.

What is claimed is:

1. A microelectrode sensing device, comprising:
   a substrate; and
   an array of microelectrode sensors formed on the substrate, each sensor comprising
   a first conductive layer, that at least partially conducts electricity, formed above the substrate and patterned to comprise a recording electrode to measure electrical activities of one or more target cells in a solution;

a second conductive layer, that at least partially conducts electricity, elevated above the first layer and patterned to comprise a plurality of positioning electrodes arranged to define a sensing region above the recording electrode in which the solution is located, the positioning electrodes operable to generate an electric field pattern in the sensing region to move and confine the target cells to a sub-region of the sensing region that at least partially overlaps the recording electrode; and an insulator material filled between the first conductive layer and the second conductive layer to electrically insulate the recording electrode from the positioning electrodes.

2. The microelectrode sensing device of claim 1, wherein the sub-region comprises locations of minimal electrical field strength.

3. The microelectrode sensing device of claim 1, wherein the sub-region is located substantially near a center of the sensing region.

4. The microelectrode sensing device of claim 1, further comprising at least four positioning electrodes.

5. The microelectrode sensing device of claim 4, wherein four of the positioning electrodes are configured to form a first pair of electrodes and a second pair of electrodes operable to
apply a first signal and a second signal to generate the electric field pattern; and
expose the target cells in the sensing region to one or more dielectrophoretic forces that are generated based on the electric field pattern.

6. The microelectrode sensing device of claim 5, wherein the first and second signals comprise a pair of alternating current signals; and
the one or more dielectrophoretic forces generated comprises a negative dielectrophoretic force.

7. The microelectrode sensing device of claim 6, wherein the first and second pairs of electrodes are configured to apply the negative dielectrophoretic force to confine the target cells into an ordered pattern of cells.

8. The microelectrode sensing device of claim 6, wherein the pair of alternating current signals comprises a signal with an amplitude of 2 volts and a frequency of 5 megahertz.

9. The microelectrode sensing device of claim 6, wherein the pair of alternating current signals applied are separated by a phase angle difference of 180 degrees.

10. The microelectrode sensing device of claim 1, wherein the positioning electrodes are further operable to generate electrical potentials based on a second-order polynomial that obeys Laplace's equation.

11. The microelectrode sensing device of claim 10, wherein the positioning electrodes have a shape based on equipotential boundaries determined based on the generated electrical potentials.

12. The microelectrode sensing device of claim 1, wherein the first conductive layer and the second conductive layer are arranged to reduce capacitive or inductive interference.

13. The microelectrode sensing device of claim 1, further comprising one or more passivation layers arranged to form barriers that at least partially confine the solution within the sensing region.

14. The microelectrode sensing device of claim 1, wherein the positioning electrodes are further operable to apply signals that selectively lyse one or more of the target cells.

15. The microelectrode sensing device of claim 1, wherein each of the sensors in the array is configured to move and confine the target cells independent of other sensors in the array.

16. The microelectrode sensing device of claim 1, wherein the recording electrode is further configured to apply a positive dielectrophoretic force.

17. The microelectrode sensing device of claim 1, further comprising a signal generator configured to apply one or more signals through the positioning electrodes or the recording electrode.

18. A method comprising:
providing a microelectrode sensing device including
forming a recording electrode in a first conductive layer, that at least partially conducts electricity, over a substrate;
arranging a plurality of positioning electrodes in a second conductive layer, that at least partially conducts electricity, over the recording electrode to define a sensing region over the recording electrode and reduce capacitive or inductive interference;
adding a passivation material at least between the first and second conductive layers arranged to electrically insulate the recording electrode from the positioning electrodes and retain one or more target cells in a solution;
using the positioning electrodes to apply an electric field pattern that moves and confines the target cells to a sub-region of the sensing region that at least partially overlaps the recording electrode; and
using the recording electrode to record electrical activities of the confined cells.

19. The method of claim 18, wherein moving and confining comprises moving and confining the target cells to a sub-region that includes locations of minimal electrical field strength.

20. The method of claim 18, wherein moving and confining comprises moving and confining the target cells substantially near a center of the sensing region.

21. The method of claim 18, further comprising arranging at least four positioning electrodes to define a sensing region.

22. The method of claim 18, further comprising
applying a pair of sinusoidal signals to generate the electric field pattern; and
exposing the target cells in the sensing region to one or more dielectrophoretic forces that are generated based on the electric field pattern.

23. The method of claim 22, wherein
applying a pair of sinusoidal signals includes applying a pair of alternating current signals; and
exposing the target cells to one or more dielectrophoretic forces includes exposing the target cells to a negative dielectrophoretic force.

24. The method of claim 23, further comprising exposing the target cells to a negative dielectrophoretic force to enable the target cells to form an ordered network of cells.

25. The method of claim 22, further comprising selecting a pair of sinusoidal signals that are separated by a phase angle difference of 180 degrees.

26. The method of claim 18, further comprising arranging the positioning electrodes to generate electrical potentials based on a second-order polynomial that obeys Laplace's equation.

27. The method of claim 26, further comprising shaping the positioning electrodes based on equipotential boundaries of the generated electrical potentials.

28. The method of claim 18, further comprising the microelectrode sensing device is used to perform at least one analysis selected from a group including impedance spectroscopy analysis, cell poration, and electrochemical analysis of physiological changes.

29. The method of claim 18, further comprising using the microelectrode sensing device to record spontaneous action potentials or evoked action potentials from one or more excitable cells.

30. The method of claim 29, wherein recording the spontaneous action potentials or evoked potentials comprises recording from neuronal cells or heart cells.

31. The method of claim 18, further comprising applying a positive dielectrophoretic force through the recording electrode.

32. A microelectrode sensing device, comprising:
a substrate; and
an array of microelectrode sensors formed on the substrate, each sensor comprising:
  a first layer formed over the substrate and patterned to comprise a sensing electrode which measures electrical activities of one or more target cells in a solution above the first layer;
  a second layer elevated above the first layer and patterned to comprise a plurality of positioning electrodes arranged to define a sensing region on top of the sensing electrode in which the solution is located, the positioning electrodes operable to generate an electric field pattern in the sensing region to move and confine the target cells above the sensing electrode; and
  an insulator material filled between the first and the second layers to electrically insulate the sensing electrode from the positioning electrodes, the insulator material shaped to define at least one channel between the first and the second layers to contain the solution, wherein the sensing region is located in the channel.

33. The microelectrode sensing device of claim 32, further comprising at least four positioning electrodes.

34. The microelectrode sensing device of claim 33, wherein
four of the positioning electrodes are configured to form a first pair of electrodes and a second pair of electrodes operable to
  apply a first signal and a second signal to generate the electric field pattern; and
  expose the target cells in the sensing region to one or more dielectrophoretic forces that are generated based on the electric field pattern.

35. The microelectrode sensing device of claim 34, wherein
the first and second signals comprise a pair of alternating current signals; and
the one or more dielectrophoretic forces generated comprises a negative dielectrophoretic force.

36. The microelectrode sensing device of claim 32, wherein the recording electrode is further configured to apply a positive dielectrophoretic force.

37. The microelectrode sensing device of claim 32, further comprising a signal generator configured to apply one or more signals through the positioning electrodes or the recording electrode.

38. A microelectrode sensing device, comprising:
a substrate; and
an array of microelectrode sensors formed on the substrate, each sensor comprising
  a first layer, that at least partially conducts electricity, formed above the substrate and patterned to comprise a recording electrode to measure electrical activities of one or more target cells in a solution;
  a second layer elevated above the first layer and patterned to comprise a plurality of positioning electrodes arranged to define a sensing region above the recording electrode in which the solution is located, the positioning electrodes operable to generate an electric field pattern in the sensing region to move and confine the target cells to a sub-region of the sensing region that at least partially overlaps the recording electrode; and
  an insulator material to electrically insulate the recording electrode from the positioning electrodes.

39. The microelectrode sensing device of claim 38, further comprising at least four positioning electrodes.

40. The microelectrode sensing device of claim 39, wherein
four of the positioning electrodes are configured to form a first pair of electrodes and a second pair of electrodes operable to
  apply a first signal and a second signal to generate the electric field pattern; and
  expose the target cells in the sensing region to one or more dielectrophoretic forces that are generated based on the electric field pattern.

41. The microelectrode sensing device of claim 40, wherein
the first and second signals comprise a pair of alternating current signals; and
the one or more dielectrophoretic forces generated comprises a negative dielectrophoretic force.

42. The microelectrode sensing device of claim 38, wherein the recording electrode is further configured to apply a positive dielectrophoretic force.

43. The microelectrode sensing device of claim 38, further comprising a signal generator configured to apply one or more signals through the positioning electrodes or the recording electrode.

* * * * *

UNITED STATES PATENT AND TRADEMARK OFFICE
CERTIFICATE OF CORRECTION

| | | |
|---|---|---|
| PATENT NO. | : 8,784,633 B2 | Page 1 of 1 |
| APPLICATION NO. | : 12/667507 | |
| DATED | : July 22, 2014 | |
| INVENTOR(S) | : Xiang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 522 days.

Signed and Sealed this
Twenty-seventh Day of October, 2015

Michelle K. Lee
*Director of the United States Patent and Trademark Office*